(12) United States Patent
Höhse et al.

(10) Patent No.: US 11,280,730 B2
(45) Date of Patent: Mar. 22, 2022

(54) BIOPROCESS CONTAINER HAVING AN OPTICAL MEASURING DEVICE

(71) Applicant: Sartorius Stedim Biotech GmbH, Göttingen (DE)

(72) Inventors: Marek Höhse, Göttingen (DE); Christian Grimm, Bad Heiligenstadt (DE); Thomas Regen, Göttingen (DE)

(73) Assignee: Sartorius Stedim Biotech GMBH, Göttingen (DE)

( * ) Notice: Subject to any disclaimer, the term of this patent is extended or adjusted under 35 U.S.C. 154(b) by 0 days.

(21) Appl. No.: 17/285,961

(22) PCT Filed: Aug. 5, 2019

(86) PCT No.: PCT/EP2019/070961
§ 371 (c)(1),
(2) Date: Apr. 16, 2021

(87) PCT Pub. No.: WO2020/088808
PCT Pub. Date: May 7, 2020

(65) Prior Publication Data
US 2021/0381969 A1  Dec. 9, 2021

(30) Foreign Application Priority Data
Oct. 31, 2018 (DE) .......................... 102018008622.5

(51) Int. Cl.
*G01J 3/00* (2006.01)
*G01N 21/51* (2006.01)
(Continued)

(52) U.S. Cl.
CPC ............ *G01N 21/51* (2013.01); *G01N 21/55* (2013.01); *G01J 3/14* (2013.01); *G01J 3/4406* (2013.01);
(Continued)

(58) Field of Classification Search
CPC ...... G01J 3/02; G01J 3/28; G01J 3/42; G01N 21/31; G01N 21/552
(Continued)

(56) References Cited

U.S. PATENT DOCUMENTS

| 2010/0017163 A1* | 1/2010 | Yamaguchi ............. G01J 5/025 |
|---|---|---|
| | | 702/99 |
| 2012/0044609 A1 | 9/2012 | Selker et al. |
| 2017/0232123 A1* | 8/2017 | Burapachaisri ........... A61L 2/10 |
| | | 422/24 |

FOREIGN PATENT DOCUMENTS

| DE | 202009010255 U1 | 10/2009 |
|---|---|---|
| DE | 102010007559 A1 | 8/2011 |

(Continued)

OTHER PUBLICATIONS

International Search Report issued in International Application No. PCT/EP2019/070961 dated Nov. 6, 2019.

*Primary Examiner* — Md M Rahman
(74) *Attorney, Agent, or Firm* — Quinn IP Law (57) ABSTRACT

The invention relates to a bioprocess container (10) having an optical measuring device (100) for non-invasive spectroscopic measurement comprising: a container housing (12), a port housing (102), which is connected to the container housing (12) and is sealed off with respect to the interior (18) of the container housing (12); at least one radiation-emitting element (124), which is designed to transmit electromagnetic radiation through the at least one fluid contained in the container housing (12); at least one radiation-receiving element (126), which is designed to at least partly receive the radiation which was transmitted by the radiation-emitting element (124); and at least one measuring insert (122), which holds and supports the at least one radiation-emitting element (124) and/or the at least one radiation-receiving element (126).

18 Claims, 6 Drawing Sheets

(51) Int. Cl.
*G01N 21/55* (2014.01)
*G01J 3/44* (2006.01)
*G01N 21/03* (2006.01)
*G01J 3/14* (2006.01)

(52) U.S. Cl.
CPC ............... *G01N 2021/0325* (2013.01); *G01N 2021/513* (2013.01)

(58) Field of Classification Search
USPC ........................................................ 356/300
See application file for complete search history.

(56) References Cited

FOREIGN PATENT DOCUMENTS

DE      102015122745 B3    1/2017
WO       2008016411 A1    2/2008

* cited by examiner

BIOPROCESS CONTAINER HAVING AN OPTICAL MEASURING DEVICE

BACKGROUND

The present invention relates to a bioprocess container with an optical measuring device for noninvasive spectroscopic measurement.

Reusable bioprocess containers, such as bioreactors or mixing containers for example, are known from the prior art. Bioreactors are containers in which specifically grown microorganisms or cells are cultured in a culture medium under the best possible controlled conditions in order to obtain the cells themselves, parts thereof or one of the metabolic products thereof. In particular, solid (biomass), liquid (culture medium) and/or gaseous (e.g., air, oxygen, carbon dioxide, nitrogen) phases can be processed in the bioreactors. In all bioprocess containers, it is, however, necessary in this connection to be able to ensure optimal conditions. To this end, various parameters in the interior of the bioreactor are usually measured or monitored with the aid of sensors which protrude into the interior of the bioreactor. Possible parameters to be measured are, for example, the pH, the $O_2$ level and the temperature of the medium contained in the bioprocess container. If parameters should deviate from predefined optimal values, the deviations can be corrected by means of appropriate measures.

One variant of a sensor for monitoring the medium is an optical sensor or an optical measuring device which measures certain parameters in the medium in a noninvasive manner by means of spectroscopy.

Before the medium or the individual constituents of the medium can be accommodated in the bioprocess container, it is necessary to sterilize the bioprocess container including the sensors mounted on the bioprocess container, such as, for example, the abovementioned optical sensor. This can be done, for example, by autoclaving or steam sterilization. Such a sterilization process, however, represents high thermal stress on the optical sensor, since even small thermal deformations can have an influence on the adjustment of the individual components of the optical sensor. Different spectroscopic techniques require different exact arrangements for optimal spectral acquisition. An exact alignment of the excitation radiation and the detection channel is required, especially in the case of transmittance measurement.

Deviations arising on the optical sensor as a result of sterilization processes are frequently corrected afterwards by statistical treatments of the spectra. However, any correction contains errors and carries the risk that undesirable deviations still exist even after the correction. Furthermore, the correction can also cause important information to be lost.

In addition, seals on the optical sensor must be exchanged after a certain number of sterilization processes. This exchange requires that the optical sensor be sent in for servicing and that it be reinstalled in the bioprocess container and reundergo fine-adjustment therein after the seals have been exchanged.

SUMMARY

It is therefore an object of the present invention to provide a bioprocess container with an optical measuring device for noninvasive spectroscopic measurement that allows prevention of thermal effects on the optical measuring device due to a sterilization process.

This object is achieved by a bioprocess container with an optical measuring device for noninvasive spectroscopic measurement, comprising:
- a container housing which is suitable for accommodating at least one fluid to be measured;
- a port housing which is connected to the container housing and is closed off from the interior of the container housing;
- at least one radiation-emitting element which is designed to transmit electromagnetic radiation through the at least one fluid contained in the container housing;
- at least one radiation-receiving element which is designed to at least partially receive the radiation which was emitted by the radiation-emitting element; and
- at least one measuring insert which holds or supports the at least one radiation-emitting element and/or the at least one radiation-receiving element, wherein the measuring insert is at least partially pushable into the port housing and is detachably connected to the port housing when pushed in.

A "noninvasive" measurement method is understood to mean a measurement method which allows measurement from outside the bioprocess container. It is not necessary for measuring apparatuses of the measuring device to penetrate into the interior of the bioprocess container. The interior of the port housing, which contains the components of the optical measuring device that are sensitive to sterilization, is not linked to the interior of the bioprocess container.

The at least one measuring insert, which holds or supports the at least one radiation-emitting element and/or the at least one radiation-receiving element, can be easily pushed into the port housing or removed from the port housing together with said elements. Therefore, during the sterilization process, the elements sensitive to sterilization have been removed from the bioprocess container. Only after the sterilization process has been completed is the measuring insert pushed into the port housing together with the at least one radiation-emitting element and/or the at least one radiation-receiving element. If the measuring insert is properly inserted in the port housing, the one radiation-emitting element and the at least one radiation-receiving element are also properly inserted, and an exact spectroscopic measurement can therefore be made. In particular, the one radiation-emitting element and the at least one radiation-receiving element are always exactly aligned in relation to one another owing to the measuring insert. A statistical correction of the spectral evaluation is therefore no longer necessary.

The port housing preferably comprises at least one window which is designed to at least partially allow electromagnetic radiation to pass between the interior of the container housing and an interior of the port housing.

The window is preferably a window surface which is part of the port housing. The window can be composed of a material which is designed to at least partially allow electromagnetic radiation to pass through. This can be achieved over the entire electromagnetic spectrum or only over a certain region of the electromagnetic spectrum. The selection of the window therefore depends on the desired measurement or on the desired spectral range to be evaluated.

It is possible to provide a window, behind which all radiation-emitting elements and radiation-receiving elements are arranged in the interior of the port housing. However, it is also possible for a window to be arranged only in front of individual radiation-emitting elements and/or radiation-receiving elements.

The window allows establishment of an optical connection between the interior of the bioprocess container and the interior of the port housing in order to be able to perform a spectroscopic measurement on the medium contained in the bioprocess container. However, there is no need to establish a fluid connection between the interior of the bioprocess container and the interior of the port housing.

Furthermore, it is preferred that the port housing has at least one measuring gap or measuring recess into which the fluid to be measured is flowable from the interior of the container housing.

An interior of the measuring gap is part of the interior of the bioprocess housing, into which some of the medium contained in the bioprocess housing can flow. The medium contained in the measuring gap can be measured by the optical measuring device by means of spectroscopy and conclusions can therefore be drawn about the entire content of the bioprocess housing.

The measuring gap preferably has at least two opposing windows which are spaced apart from one another such that the measuring gap is formed between the windows.

In other words, two opposing faces of the port housing that form the measuring gap are at least regionally formed as windows, as already described above. The two opposing windows enable electromagnetic radiation to be transmitted through the measuring gap as part of the spectroscopic measurement.

The measuring gap is preferably formed by a radiation deflection device,
  wherein the radiation deflection device has at least one first deflection element and at least one second deflection element,
  wherein the first and second deflection elements are arranged opposite one another and are at least regionally spaced apart from one another, so that the measuring gap is formed between the first and second deflection elements.

Alternatively, a radiation deflection device can be connected to the measuring insert and be pushable into the port housing together with the measuring insert,
  wherein the radiation deflection device has at least one first deflection element and at least one second deflection element,
  wherein the first and second deflection elements are arranged such that they are spaced apart by the at least two windows and the measuring gap.

In contrast to the above-described embodiment in which the measuring gap is defined by the first and second deflection elements, the measuring gap is formed by at least two opposing windows in this embodiment. Properties of such a window have already been described above. The port housing is therefore preferably designed such that the first and second deflection elements are arrangeable in the interior of the port housing and are preferably connected to the measuring insert. As a result, the first and second deflection elements can likewise be removed from the port housing and reinserted with the measuring insert.

The first deflection element is preferably designed to receive electromagnetic radiation which is emitted by the radiation-emitting element and to then deflect it to the second deflection unit such that the radiation passes through the measuring gap, and
  wherein the second deflection unit is designed to receive the radiation from the first deflection unit and to then deflect it to the radiation-receiving element.

The first deflection element receives the electromagnetic radiation from the radiation-emitting element from a first direction and deflects the radiation into a second direction, so that the radiation passes through the measuring gap. The first direction is different from the second direction. The second deflection element receives at least part of the radiation from the first deflection element and deflects the radiation such that the radiation is retransmitted in the first direction to the radiation-receiving element. Optionally, a pinhole aperture can be introduced into the beam path. Such a configuration of the radiation-emitting element and the radiation-receiving element therefore makes it possible to carry out a transmittance measurement.

The first and second deflection elements are made of a material penetrable for electromagnetic radiation; either over the entire electromagnetic spectrum or only for one or more particular spectral regions.

The first and second deflection elements are not critical elements, which can be exposed to thermal stress during a sterilization process without causing possible errors in the subsequent measurement result. They can therefore remain on the bioprocess container during the sterilization process.

In a preferred embodiment, the first deflection element is designed to receive electromagnetic radiation which is emitted by the radiation-emitting element and to then deflect it to the measuring gap, and
  wherein a radiation-receiving element is arranged below the measuring gap.

The radiation-receiving element below the measuring gap is designed to measure the portion of the electromagnetic radiation that is radiated to the radiation-receiving element after reaction or contacting with the medium in the measuring gap. A 90° detection is preferably concerned here.

Such a configuration can be an embodiment of its own in which the second deflection element then has no function. Here, the second deflection element merely delimits the measuring gap.

Such a configuration can, however, also be effected in addition to the transmittance measurement already described above. This means that multiple radiation-receiving elements are present here.

The radiation-emitting element and the radiation-receiving element are preferably arranged at the same position below the measuring gap.

Such an arrangement of the radiation-emitting element and the radiation-receiving element makes a reflection measurement (e.g., Raman spectroscopy, fluorescence spectroscopy, UV-Vis spectroscopy or near-infrared spectroscopy) possible. In other words, electromagnetic radiation is emitted by the radiation-emitting element in the direction of the measuring gap and reflected there by the medium contained in the measuring gap. The radiation-receiving element can measure this reflected portion, the radiation-receiving element being located at the same position as the radiation-emitting element. The radiation-emitting element and the radiation-receiving element are preferably designed as one unit.

Alternatively, it is also possible for the radiation-emitting element and the radiation-receiving element to be located at the same position below the first deflection element in order to measure the portion reflected by the medium.

Furthermore, a face of the second deflection element that faces the measuring gap can be at least regionally diffusely scattering,
  wherein the first deflection element is designed to receive electromagnetic radiation which is emitted by the radiation-emitting element and to then deflect it to the measuring gap and/or the diffusely scattering face of the second deflection element, and the radiation-receiving element can be arranged such that it can measure the electromagnetic radiation which is reflected by the fluid to be measured and/or the diffusely scattering face.

This embodiment makes a transflection measurement (reflection of the electromagnetic radiation on the diffusely scattering face) and/or a reflection measurement (reflection of the electromagnetic radiation on the medium) possible.

The radiation-emitting element and the radiation-receiving element are preferably located below the first deflection element. Similar to the reflection measurement described above, the two elements can also be designed as one unit here. In particular, the radiation-emitting element and the radiation-receiving element are preferably arranged at the same position.

Preferably, the first and second deflection elements are each a prism or each have a radiation-reflecting face.

If the first and second deflection elements have a radiation-reflecting face, a face of the first and second deflection elements is at least regionally coated with a reflective material, such as gold for example. The face is oriented such that the electromagnetic radiation is deflectable from the first to the second direction and vice versa. In other words, the reflective face forms a deflection mirror.

Furthermore, it is preferred that the first and second deflection elements are arranged on at least one window.

The at least one window is preferably not completely covered by the first and second deflection elements. For example, a base face of the measuring gap is not covered by the first and second deflection elements. In this case, multiple measuring methods can be combined within one optical measuring device (see, for example, the reflection measurement or transflection measurement described above).

In particular, a first radiation-emitting element and a first radiation-receiving element could be positioned with the aid of the measuring insert such that a transmittance measurement could be effected via the first and second deflection elements. However, at the same time, a second radiation-emitting element and a second radiation-receiving element could be positioned with the aid of the measuring insert below the base face of the measuring insert (face with window only) such that a reflection measurement (e.g., Raman spectroscopy, fluorescence spectroscopy, UV-Vis spectroscopy or near-infrared spectroscopy) can be effected in parallel via the base face of the measuring gap.

According to a preferred embodiment, the measuring insert has at least one holding recess into which the radiation-emitting element or the radiation-receiving element is insertable.

What is made possible by the holding recesses for the radiation-emitting element and/or the radiation-receiving element is that said elements are always situated in an optimal position or alignment once the measuring insert has been inserted into the port housing. In particular, the radiation-emitting element and the radiation-receiving element can be inserted into the port housing together or at the same time owing to the measuring insert with holding recesses. This means a saving of time and costs.

Preferably, the measuring insert is clampable into the port housing, lockable into place with the port housing and/or screwable to the port housing.

Such detachable connections between the measuring insert and the port housing mean that the measuring insert can be easily connected to the port housing and can also be easily detached and removed before a sterilization process. Furthermore, the measuring insert is securely connected to the port housing by the abovementioned connection types.

It is further preferred that the measuring insert comprises:
at least one holding face in which the at least one holding recess is formed and which is arranged opposite a window, a first deflection element and/or a second deflection element when insertion into the port housing has taken place, and
at least one connecting face which is connected to the at least one holding face and is designed to be connected to the port housing when insertion has taken place.

"When insertion has taken place" is understood to mean the state in which the measuring insert is completely inserted into the port housing or has occupied such a position in the port housing that the optical measuring insert is ready for spectroscopic measurement.

The at least one holding face is preferably aligned such that it is arranged parallel to a window, a first deflection element and/or a second deflection element.

The at least one connecting face is connected to the at least one holding face and is preferably aligned such that it, when the measuring insert is inserted, comes into contact with an inner face of the port housing, at least regionally, in order to be detachably connected to the port housing.

The bioprocess container is preferably a bioreactor.

As a reusable bioreactor, the bioreactor can, for example, be made of glass or steel. However, it is also conceivable that the bioprocess container is a mixing container in which no culturing takes place, but at least one fluid is mixed, but where it is necessary to monitor the individual status parameters of the fluid. Alternatively, it can be a storage container for at least one fluid. Both the mixing container and the storage container are preferably made of glass or steel.

Preferably, the port housing at least partially protrudes into the interior of the container housing.

According to a further aspect of the present invention, the present technical object is achieved by an optical measuring device for noninvasive spectroscopic measurement for a bioprocess container, comprising:
a port housing which is connectable to a container housing of the bioprocess container and is designed such that it is closed off from the interior of the container housing when connected;
at least one radiation-emitting element which is designed to transmit electromagnetic radiation through at least one fluid contained in the container housing;
at least one radiation-receiving element which is designed to at least partially receive the radiation which was emitted by the radiation-emitting element; and
at least one measuring insert which holds or supports the at least one radiation-emitting element and/or the at least one radiation-receiving element,
wherein the measuring insert is at least partially pushable into the port housing and is detachably connected to the port housing when pushed in.

The port housing preferably comprises at least one window which is designed to at least partially allow electromagnetic radiation to pass between the interior of the container housing and an interior of the port housing.

Furthermore, it is preferred that the port housing has at least one measuring gap or measuring recess into which the fluid to be measured is flowable from the interior of the container housing.

The measuring gap preferably has at least two opposing windows which are spaced apart from one another such that the measuring gap is formed between the windows.

Furthermore, it is preferred that the measuring gap is formed by a radiation deflection device, wherein the radiation deflection device has at least one first deflection element and at least one second deflection element, wherein the first and second deflection elements are arranged opposite one another and are at least regionally spaced apart from one another, so that the measuring gap is formed between the first and second deflection elements.

The first deflection element is preferably designed to receive electromagnetic radiation which is emitted by the radiation-emitting element and to then deflect it to the second deflection unit such that the radiation passes through the measuring gap, and wherein the second deflection unit is designed to receive the radiation from the first deflection unit and to then deflect it to the radiation-receiving element.

Furthermore, it is preferred that the first deflection element is designed to receive electromagnetic radiation which is emitted by the radiation-emitting element and to then deflect it to the measuring gap, and that a radiation-receiving element is arranged below the measuring gap.

The radiation-emitting element and the radiation-receiving element are preferably arranged at the same position below the measuring gap.

Preferably, a face of the second deflection element that faces the measuring gap is at least regionally diffusely scattering, wherein the first deflection element is designed to receive electromagnetic radiation which is emitted by the radiation-emitting element and to then deflect it to the measuring gap and/or the diffusely scattering face of the second deflection element, and wherein the radiation-receiving element is arranged such that it can measure the electromagnetic radiation which is reflected by the fluid to be measured and/or the diffusely scattering face Preferably, the first and second deflection elements each have a prism or each have a radiation-reflecting face.

It is preferred that the first and second deflection elements are arranged on at least one window.

The measuring insert preferably has at least one holding recess into which the radiation-emitting element or the radiation-receiving element is insertable.

Furthermore, it is preferred that the measuring insert is clampable into the port housing, lockable into place with the port housing and/or screwable to the port housing.

The measuring insert preferably comprises:

at least one holding face in which the at least one holding recess is formed and which is arranged opposite a window, a first deflection element and/or a second deflection element when insertion into the port housing has taken place, and at least one connecting face which is connected to the at least one holding face and is designed to be connected to the port housing when insertion has taken place.

Preferably, the port housing when connected at least partially protrudes into the interior of the container housing.

These and other goals, features and advantages of the present invention will become clearer by study of the following detailed description of preferred embodiments and of the appended drawings. Furthermore, it is pointed out that, although embodiments are described separately, individual features of said embodiments can be combined to form additional embodiments.

DETAILED DESCRIPTION

FIGS. 1a) and 1b) show a first embodiment of an optical measuring device 100 which is inserted into a bioprocess container 10. The bioprocess container 10 is preferably a bioreactor, mixing container or storage tank preferably composed of steel or glass. The bioprocess container 10 is designed to accommodate at least one fluid that is to be measured or monitored by the optical measuring device 100.

For insertion of the optical measuring device 100 into the bioprocess container 10 or for connection thereof to the bioprocess container 10, a container housing 12 has a container housing cutout 14. The shape and size of the container housing cutout 14 is designed such that the optical measuring device 100 is insertable from an exterior 16 of the container housing 12 in the direction of an interior 18 of the container housing 12. The container housing cutout 14 is preferably circular. In particular, it is preferred that the optical measuring device 10 is insertable into the bioprocess container 10 such that the optical measuring device 10 at least partially protrudes into the interior 18 of the bioprocess container 10.

The optical measuring device 100 comprises a port housing 102 which can accommodate optical measuring instruments and the interior 104 thereof is designed such that it is fluid-tight with respect to the interior 18 of the container housing 12. The container housing 12 preferably has a container housing projection 20 which projects from a lateral surface 22 of the container housing 12 along the container housing cutout 14 in the direction of the interior 18 of the container housing 12. The container housing projection 20 preferably protrudes perpendicularly from the lateral surface 22 of the container housing 12. The port housing 102 in turn likewise has a lateral surface 106 and at least partially overlaps with the container housing projection 20 when inserted. As shown in FIG. 1b), which shows a sectional view along the sectional axis B-B from FIG. 1a), the lateral surface 106 of the port housing 102 can project over the container housing projection 20 into the interior 18 of the container housing 12. To ensure that the bioprocess container 10 is fluid-tight and that no fluid can escape via the container housing cutout 14, it is advantageous to arrange at least one sealing ring 24 between the container housing projection 20 and the lateral surface 106 of the port housing 102.

At a front end 108 of the port housing 102 that protrudes into the interior 104 of the port housing 102, at least one window 110 can be formed at least regionally. The at least one window 110 can be composed of glass or plastic and can be transparent to electromagnetic radiation over the entire spectrum or only over some spectral regions or one spectral region. The window 110 makes it possible for optical measuring instruments to have noninvasive access to the interior 18 of the container housing 12, but for the interior 104 of the port housing 102 to be fluid-tight with respect to the interior 18 of the container housing 12.

As shown in FIG. 1b), the window 110 extends over the entire front end 108 of the port housing 102.

In order to be able to carry out a transmittance measurement, the optical measuring device 100 preferably has a measuring gap 112. The measuring gap 112 is preferably formed by two prisms 114 (deflection elements). The prisms 114 are arranged on the window 110 and are spaced apart from one another such that the desired measuring gap 112 is formed between the prisms 114. The measuring gap 112 is in fluid connection with the interior 18 of the container housing 12, so that a partial amount of the fluid can flow from the container housing 12 into the measuring gap 112 and can be measured there as a reference amount for the remaining content of the container housing 12. As shown in FIG. 1b), the prisms 114 preferably have a triangular shape in a sectional view. A right triangle is preferably concerned. The face 118 of the prism 114 that is opposite the face enclosing the measuring gap 112 is arranged at an incline with respect to an axis of rotation R of the port housing 102.

Alternatively, the measuring gap 112 can also be formed by transparent elements (not shown here) which have a similar shape to the prisms 114. The transparent elements can have material properties like the window 110. However, in contrast to the prisms 114, the transparent elements have a reflective coating, at least regionally, on the inclined face 118 (inclined with respect to the axis of rotation R of the port housing 102).

Although FIG. 1b) shows a window 110 which closes the port housing 102 at the front end 108, the prisms 114 or the transparent elements can also directly close the front end 108 of the port housing 102. A base face 120 of the measuring gap 112 can then be designed as a window 110 or else be nontransparent, similar to the lateral surface 104 of the port housing 102.

A rear end 116 of the port housing 102 is preferably open to the exterior of the port housing 102. At least one measuring insert 122 is at least partially pushable into the interior 104 of the port housing 102 via said open rear end 116. FIG. 1b) shows the measuring insert 122 when inserted. The measuring insert 122 is detachably connected to the port housing 102, so that the measuring insert 122 can be easily removed from the port housing 102 during a sterilization process and is subsequently reinsertable into the port housing 102.

Figure 1:
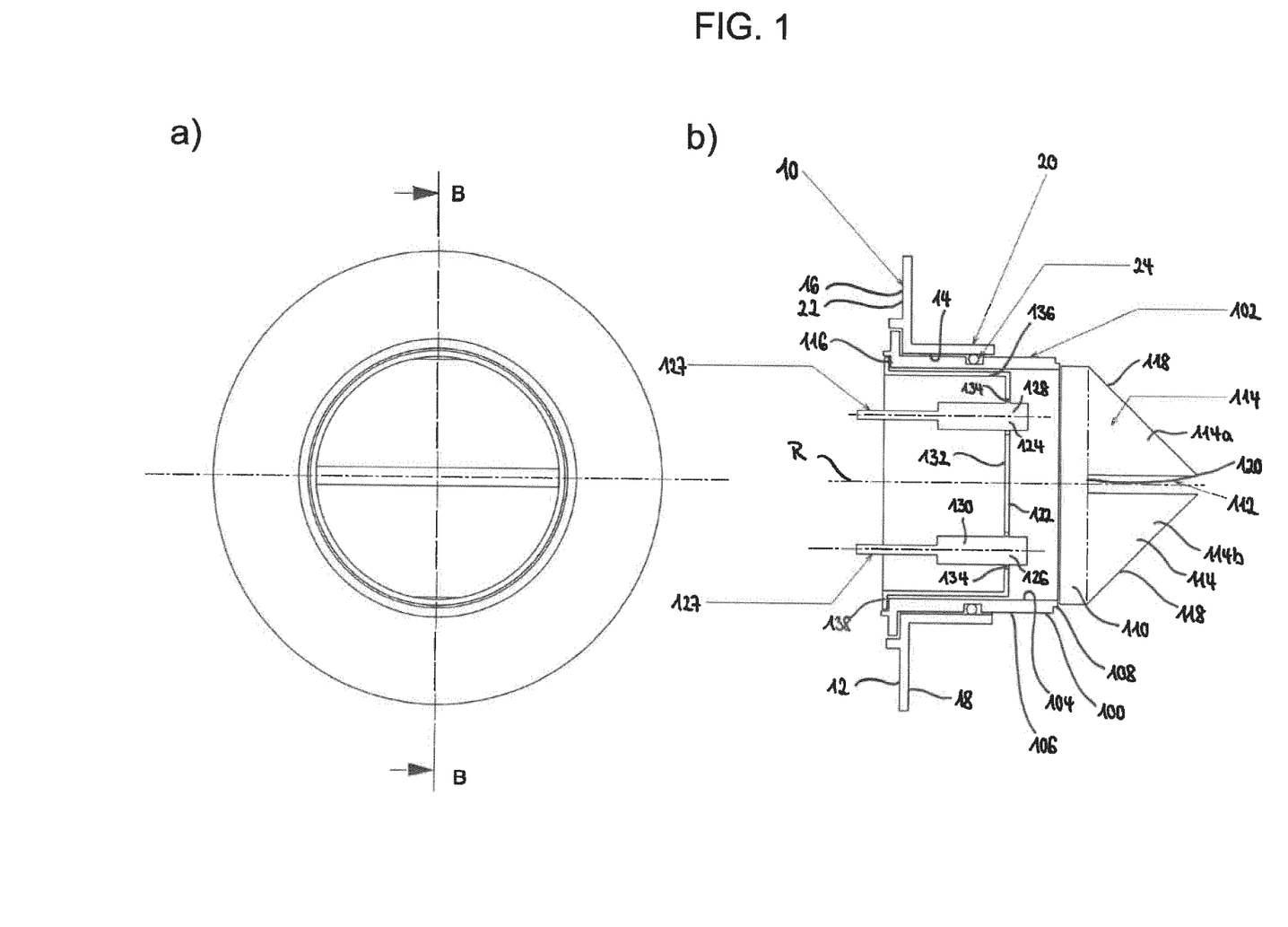
FIG. 1a) shows a top view of a subregion of a container housing of a bioprocess container with an optical measuring device according to a first embodiment.
FIG. 1b) shows a sectional view along the sectional axis B-B in FIG. 1a)
Figure 4:
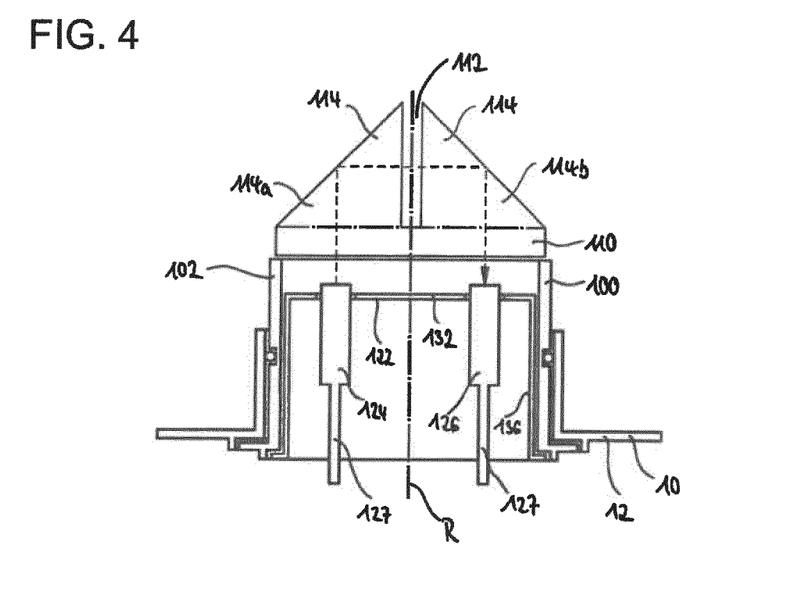
FIG. 4 shows FIG. 1b) with a drawn-in course of the electromagnetic radiation.

The measuring insert from FIG. 1 is advantageously suitable for transmittance measurement. In particular, the measuring insert 122 is designed such that it can hold or support at least one radiation-emitting element 124 and/or at least one radiation-receiving element 126. FIG. 1b) shows one embodiment with a measuring insert 122 which holds a radiation-emitting element 124 and a radiation-receiving element 126. The radiation-emitting element 124 is designed to emit electromagnetic radiation, whereas the radiation-receiving element 126 is designed to receive electromagnetic radiation. The radiation-emitting element 124 preferably has at least one light guide 127. At least one radiation element (not shown here), such as at least one LED for example, electromagnetic radiation can be emitted via the at least one light guide 127 via the radiation-emitting element 124. The radiation-emitting element 124 preferably has a radiation out-coupling element 128 at a front end. The electromagnetic radiation can exit or be coupled out from the radiation-emitting element 124 via the radiation out-coupling element 128. The radiation-emitting element 124 is preferably arranged with the aid of the measuring insert 122 such that the electromagnetic radiation can be emitted or coupled out parallel to the axis of rotation R of the port housing 102 and can be transmitted to a first prism 114a (first deflection element). The electromagnetic radiation which strikes the first prism 114a is deflected by the first prism 114a such that the electromagnetic radiation radiates through the measuring gap 112 and at least partially strikes the second prism 114b (second deflection element). The electromagnetic radiation is at least partially absorbed and/or reflected in the measuring gap 112 by the medium contained in the measuring gap 112. Thus, only a portion of the emitted electromagnetic radiation reaches the second prism 114b. The second prism 114b in turn deflects the electromagnetic radiation such that the electromagnetic radiation is transmitted to the radiation-receiving element 126. The radiation-receiving element 126 preferably comprises a radiation in-coupling element 130 via which the received radiation can be coupled in. At least one light guide 127 guides the received radiation to a photodetector (not shown here) suitable for receiving and evaluating the received radiation. By means of the measuring insert 122, the radiation-receiving element 126 is preferably arranged in the port housing 102 such that the electromagnetic radiation can radiate parallel to the axis of rotation R of the port housing 102 from the second prism 114b to the radiation-receiving element 126. FIG. 4 show FIG. 1b) with a drawn-in course of the electromagnetic radiation.

The measuring insert 122 preferably has at least one holding face 132 which is preferably aligned perpendicular to the axis of rotation R of the port housing 102 when insertion has taken place. The holding face 132 has at least one holding recess 134 into which a radiation-emitting element 124 or a radiation-receiving element 126 is respectively insertable. Said elements 124, 126 can be screwable into the holding recess 134 or be held in the holding recess 134 by a press fit. As shown in FIG. 1b), the radiation out-coupling element 128 and the radiation in-coupling element 130 are preferably held by the measuring insert 122.

Furthermore, the measuring insert 122 has at least one connecting face 136. The connecting face 136 preferably extends from the holding face 132 at least regionally parallel to the axis of rotation R of the port housing 102 and is at least regionally in contact with the lateral surface 106 of the port housing 102 when the measuring insert 122 is inserted. The connecting face 136 is detachably connectable to the lateral surface 106 of the port housing 102, so that the measuring insert 122 can be easily removed from the port housing 102 during a sterilization process. The connecting face 136 can have, for example, at least one rubber ring (not shown here) which establishes a stable connection between the measuring insert 122 and the port housing 102. As an alternative or in addition, the measuring insert can be screwable into the port housing 102. A rear end 138 of the connecting face 136 is designed as a free end and can, as shown in FIG. 1b), be angled in relation to the rest of the connecting face 136. The rear end 138 of the connecting face 136 preferably extends perpendicular to the axis of rotation R of the port housing 102. Said rear end 138 can be used to avoid the measuring insert being too deeply insertable into the port housing 102.

Without insertion having taken place, the connecting face 136 of the measuring insert 122 could also be designed such that the connecting face 136 widens from the holding face 132 toward the rear end 138 of the connecting face 136. As a result, the measuring insert 122 forms a kind of clamp which, by compression of the rear end 138 of the connecting faces 136, allows insertion of the measuring insert 122 into the port housing 102. The measuring insert 122 is thus clamped into the port housing 102.

The measuring insert 122 is preferably made of metal or plastic.

FIGS. 2a) and 2b) show a second embodiment of an optical measuring device 100. However, only the parts of the optical measuring device 100 that differ from the first embodiment are described below. The description of the remaining parts of the optical measuring device 100 accordingly also applies to the second embodiment.

Figure 2:
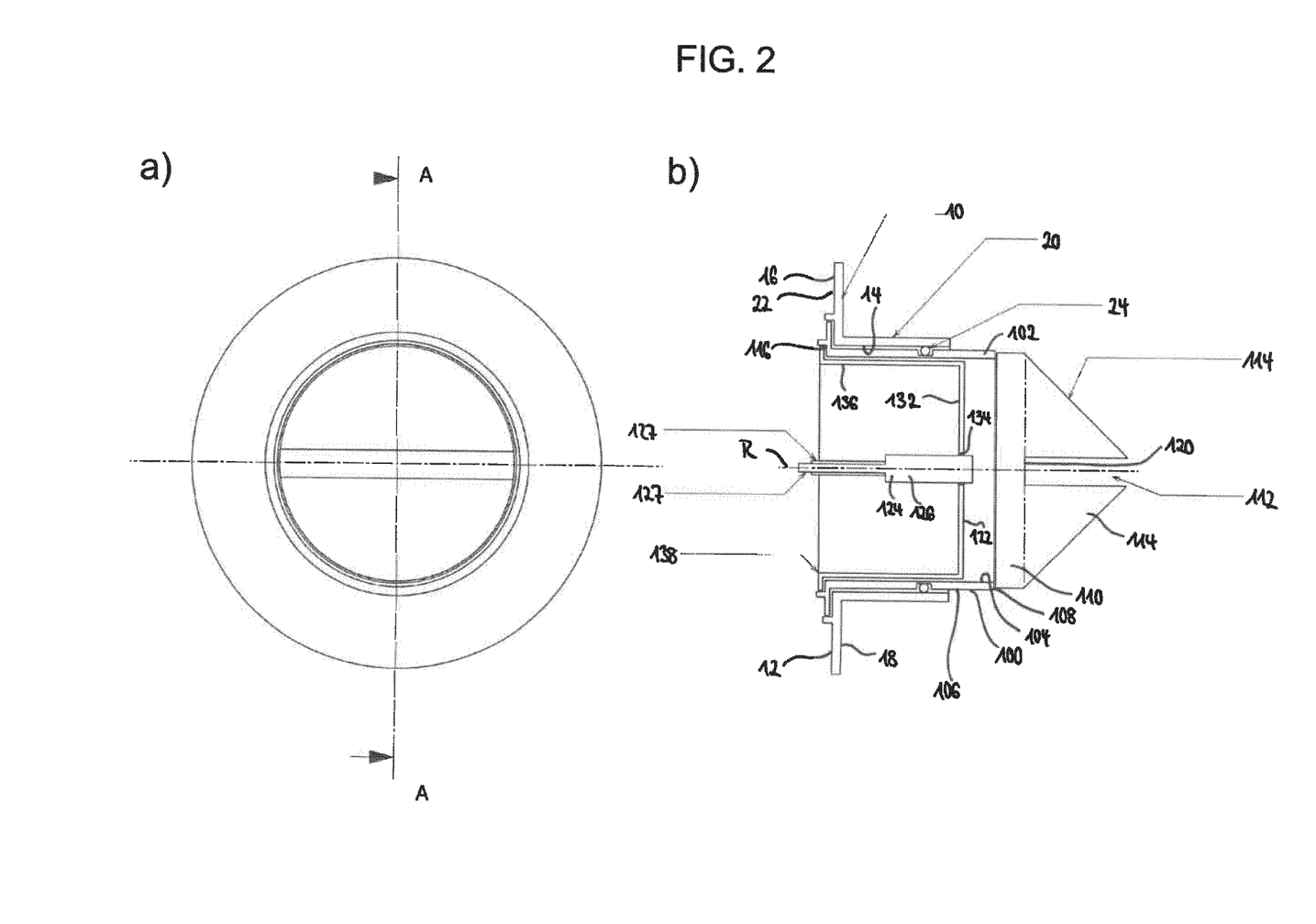
FIG. 2a) shows a top view of a subregion of a container housing of a bioprocess container with an optical measuring device according to a second embodiment.
FIG. 2b) shows a sectional view along the sectional axis A-A in FIG. 2a)
Figure 5:
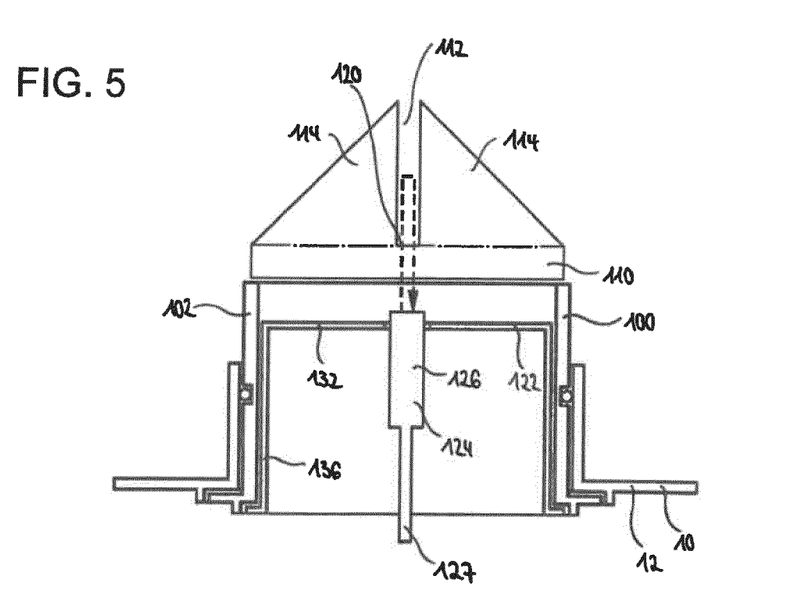
FIG. 5 shows FIG. 2b) with a drawn-in course of the electromagnetic radiation.

In contrast to the optical measuring device 100 from FIGS. 1a) and 1b), the optical measuring device 100 from FIGS. 2a) and 2b) is suitable for reflection measurement (e.g., Raman spectroscopy). To this end, electromagnetic radiation is emitted by the radiation-emitting element 124, preferably parallel to the axis of rotation R of the port housing 102. The electromagnetic radiation is then reflected and/or absorbed by the medium situated in the bioprocess container 10. However, only the portion of the electromagnetic radiation that is reflected by the medium is measured. To this end, the radiation-receiving element 126 is preferably located at the same site as the radiation-emitting element 124. In other words, what is received in turn by the radiation-receiving element 126 is radiation which is reflected from the medium to the radiation-receiving element 126 preferably parallel to the axis of rotation R of the port housing 102. It is not absolutely necessary for the optical measuring device 100 to have a measuring gap 112. However, as shown in FIGS. 2a) and 2b), a measuring gap 112 can be provided. When the measuring insert 122 is inserted, the radiation-emitting element 124 and the radiation-receiving element 126 are preferably arranged such that the electromagnetic radiation can radiate through the base face 120 of the measuring gap 112. It is crucial that the base face 120 is designed as a window 110 at least regionally. If the optical measuring device 100 does not have a measuring gap 112, the radiation-emitting element 124 and the radiation-receiving element 126 can, in comparison with FIG. 2, also be arranged with parallel displacement in relation to the axis of rotation R of the port housing 102. What is crucial here is merely that said elements are arranged below a window 110. FIG. 5 show FIG. 2b) with a drawn-in course of the electromagnetic radiation.

The radiation out-coupling element 128 and the radiation in-coupling element 130 are preferably combined, as shown in FIG. 2b). The light guides 127 of the radiation-emitting element 124 and of the radiation-receiving element 126 are preferably bundled to form a fiber bundle.

In order to be able to calibrate the radiation-receiving element 126 for reflection measurement, especially for calibration of the photodetector, a further radiation-emitting element (not shown here) can be arranged in the measuring insert 122 parallel to the direction of rotation R of the port housing 102 and laterally offset in relation to the radiation-receiving element 126. In this case, the measuring gap 112 is delimited by at least one deflection element, below which the further radiation-emitting element is arranged. Here too, the measuring gap 112 can, for example, be formed by two deflection elements, as shown in FIG. 1 for example. Alternatively, the second deflection element can, however, also be replaced by a delimitation element without a deflection function.

FIGS. 3a) and 3b) show a third embodiment of an optical measuring device 100. Here, various measuring methods can be easily combined together in one optical measuring device 100 with the aid of the measuring insert 122.

Figure 6:
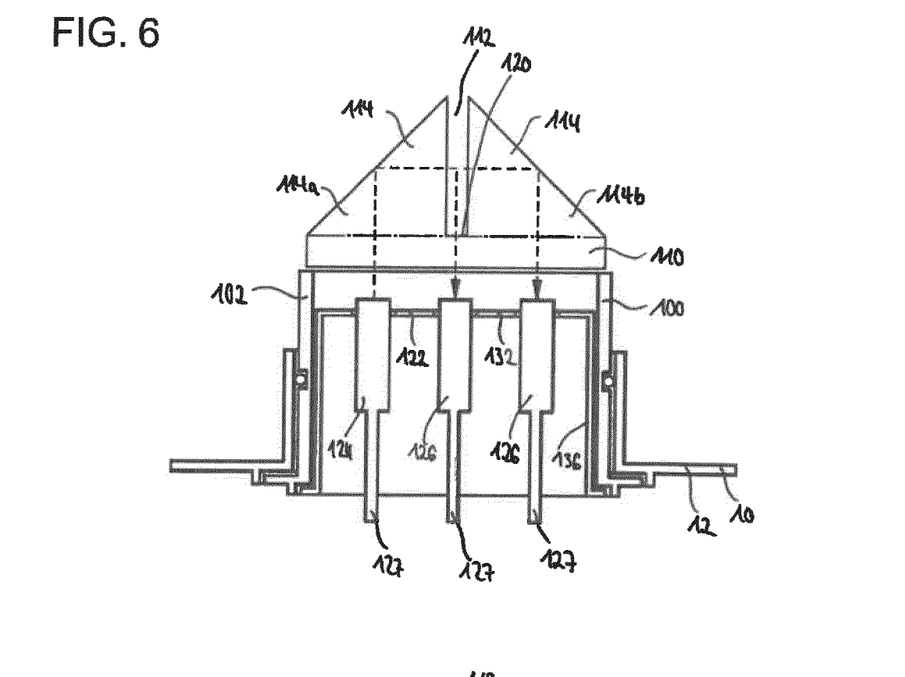
FIG. 6 shows FIG. 3b) with a drawn-in course of the electromagnetic radiation; container with an optical measuring device with a 90° detection.

Specifically, in the third embodiment, what can be carried out is, firstly, the transmittance measurement described with regard to FIG. 1. However, what is additionally located here below the measuring gap 112 is a further radiation-receiving unit 126 which is designed to receive electromagnetic radiation that is deflected or diverted by the medium in the measuring gap 112 or is radiated after contact with the medium. A 90° detection is preferably concerned here. FIG. 6 show FIG. 3b) with a drawn-in course of the electromagnetic radiation.

Figure 7:
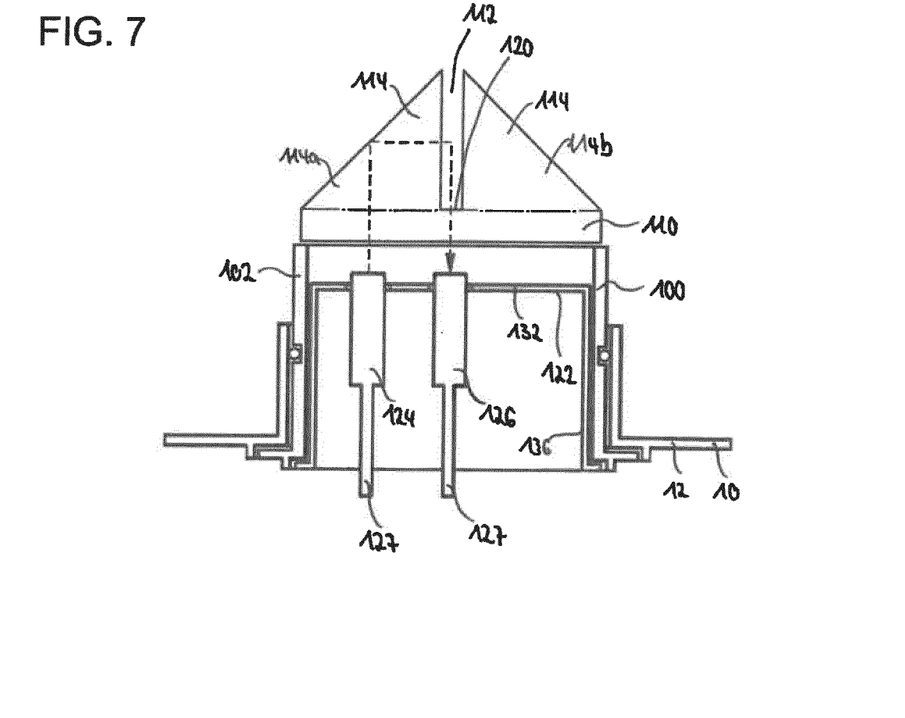

With regard to the embodiment from FIG. 3, it is furthermore conceivable that at least one radiation-receiving element 126 is arranged only below the measuring gap 112. This means that no transmittance measurement is carried out; instead, what is detected is measured is only the portion of the electromagnetic radiation that is radiated to the radiation-receiving element 126 below the measuring gap 112 after contact with the medium. FIG. 7 shows a sectional view through part of a bioprocess container 10 with an optical measuring device 100, in which the course of the electromagnetic radiation is drawn in for a 90° detection. As is apparent from the drawing, the second deflection element merely delimits of the measuring gap 112 here. The electromagnetic radiation is not deflected.

Figure 3:
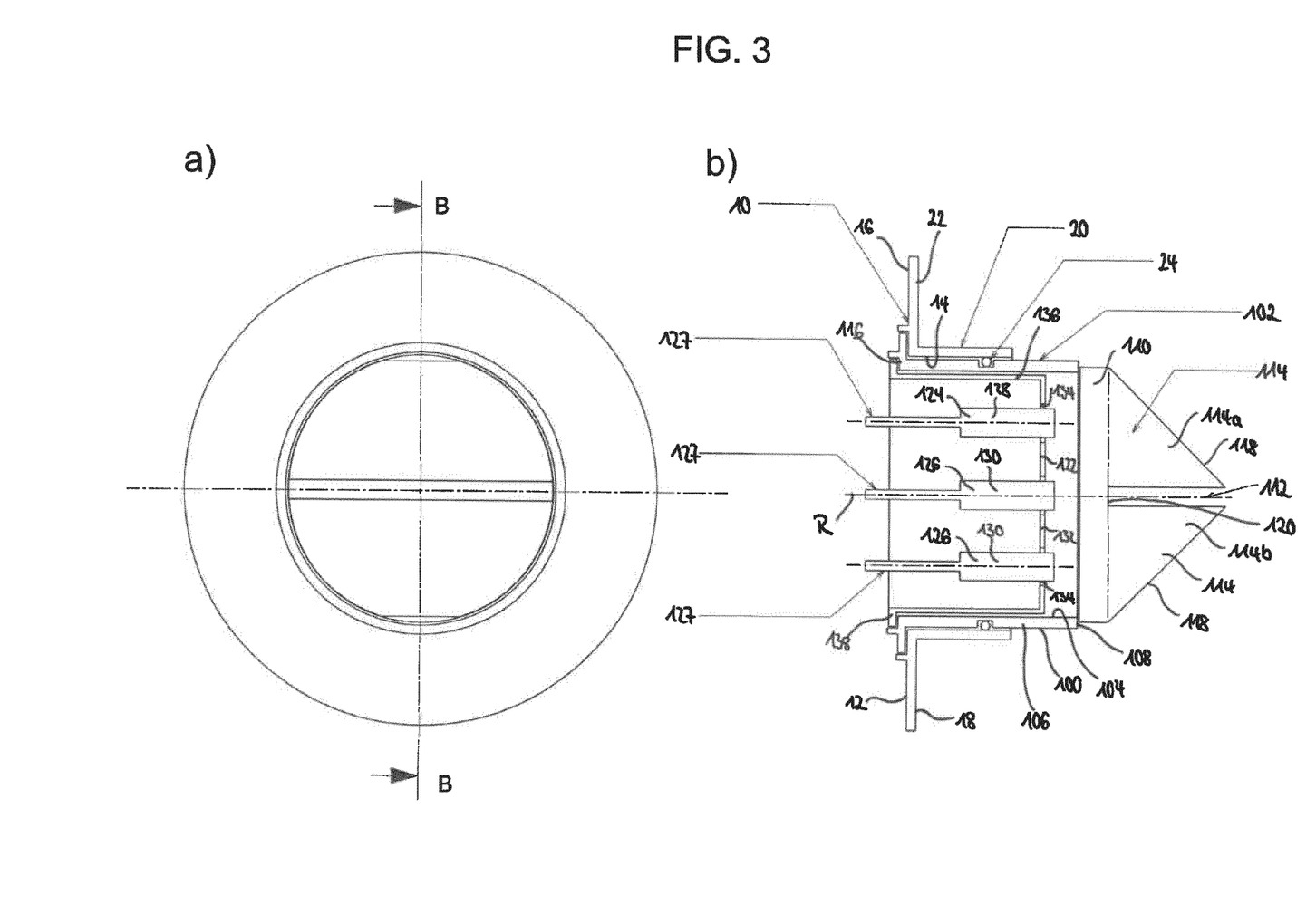
FIG. 3a) shows a top view of a subregion of a container housing of a bioprocess container with an optical measuring device according to a third embodiment.
FIG. 3b) shows a sectional view along the sectional axis B-B in FIG. 3a).
Figure 8:
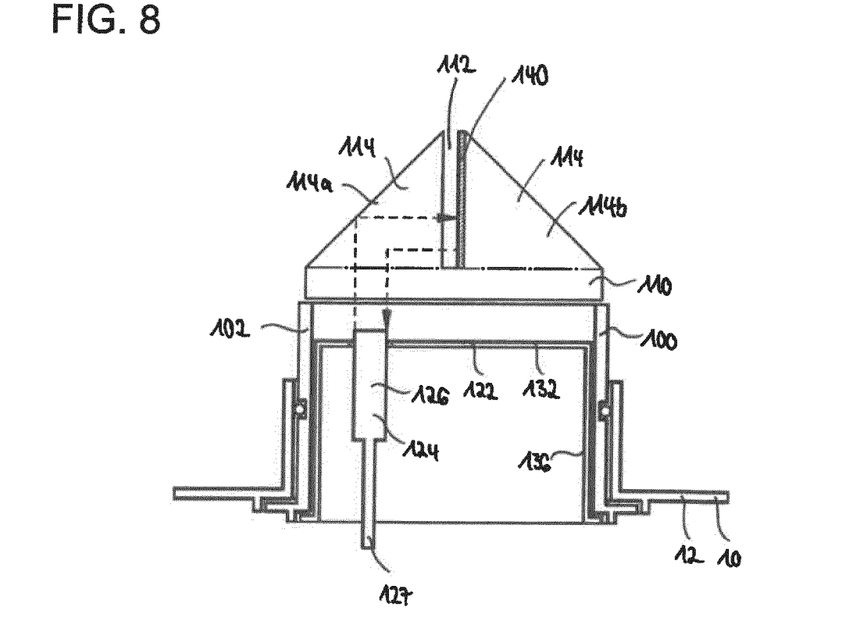
FIG. 8 shows a sectional view through part of a bioprocess container with an optical measuring device with a transflection measurement.

Furthermore, the arrangement shown in FIG. 3 can likewise be advantageously used for a transflection measurement. To this end, the face of the second prism 114b or the second deflection element that faces the measuring gap 112 is designed as a diffusely scattering surface 140 at least regionally. At least part of the electromagnetic radiation passing through the measuring gap 112 is reflected on this diffusely scattering surface 140 and can then be received or detected by a radiation-receiving element 126 located below the first prism 114a. FIG. 8 shows a sectional view through part of a bioprocess container 10 with an optical measuring device 100, in which the course of the electromagnetic radiation is drawn in for a transflection measurement.

In both the first and the third embodiment, the measuring gap 112 is formed by the prisms 114 which come into contact with the medium in the container housing 12. The prisms 114 remain in the bioprocess container 10 during the sterilization process, whereas the measuring insert 122 is removed from the port housing 102. However, it is also conceivable that the prisms 114 or the transparent elements are arranged in the interior 104 of the port housing 102 and are preferably connected to the measuring insert 122. The prisms 114 or the transparent elements can thus also be removed from the port housing 102 during the sterilization process. The prisms 114 or the transparent elements could be attached to the measuring insert 122 with the aid of spacers.

In order to form a measuring gap 112, the front end 108 of the port housing 102 could have a measuring gap 112. In particular, the front end 108 of the port housing 102 could have a first projection and a second projection, into which a prism 114 or a transparent element respectively protrudes. The faces of the projections which lie opposite one another and enclose the measuring gap 112 are designed as windows 110 at least regionally.

Although the transparent elements and the prisms 114 in the embodiments shown consist of two parts, these deflection elements could also be composed of a specially manufactured piece that allows, for example, a laterally shifted 180° reflection. In this case, the measuring insert 122 could be directly oriented by structures in the deflection elements (e.g., by pins or grooves).

In the abovementioned embodiments, the window 110 is described as a transparent element that is transparent to electromagnetic radiation. However, it is also conceivable that the window 110 is a more complex optical system that is, for example, suitable for microscopy.

Embodiment 2 shows an embodiment in which multiple measuring techniques are combined in one optical measuring device. It is furthermore possible that various measuring techniques can be combined via the kind of light guides 127 chosen.

LIST OF REFERENCE SIGNS

10 Bioprocess container
12 Container housing
14 Container housing cutout
16 Exterior of the container housing
18 Interior of the container housing
20 Container housing projection
22 Lateral surface of the container housing
24 Sealing ring
100 Optical measuring device
102 Port housing
104 Interior of the port housing
106 Lateral surface of the port housing
108 Front end of the port housing
110 Window
112 Measuring gap
114 Prism
114a First prism
114b Second prism
116 Rear end of the port housing
118 Inclined face
120 Base face of the measuring gap
122 Measuring insert
124 Radiation-emitting element
126 Radiation-receiving element
127 Light guide
128 Radiation out-coupling element
130 Radiation in-coupling element
132 Holding face
134 Holding recess
136 Connecting face
138 Rear end of the connecting face
140 Diffusely scattering surface
R Axis of rotation of the port housing

The invention claimed is:

1. A bioprocess container with an optical measuring device for noninvasive spectroscopic measurement, comprising:
a container housing which is suitable for accommodating at least one fluid to be measured;
a port housing which is connected to the container housing and is closed off from the interior of the container housing;
at least one radiation-emitting element which is designed to transmit electromagnetic radiation through the at least one fluid contained in the container housing;
at least one radiation-receiving element which is designed to at least partially receive the radiation which was emitted by the radiation-emitting element; and
at least one measuring insert which holds or supports the at least one radiation-emitting element and/or the at least one radiation-receiving element,
wherein the measuring insert is at least partially pushable into the port housing and is detachably connected to the port housing when pushed in.

2. The bioprocess container as claimed in claim 1, wherein the port housing comprises at least one window which is designed to at least partially allow electromagnetic radiation to pass between the interior of the container housing and an interior of the port housing.

3. The bioprocess container as claimed in claim 1, wherein the port housing has at least one measuring gap or measuring recess into which the fluid to be measured is flowable from the interior of the container housing.

4. The bioprocess container as claimed in claim 3, wherein the measuring gap has at least two opposing windows which are spaced apart from one another such that the measuring gap is formed between the windows.

5. The bioprocess container as claimed in claim 4, wherein a radiation deflection device is connected to the measuring insert and is pushable into the port housing together with the measuring insert,
wherein the radiation deflection device has at least one first deflection element and at least one second deflection element,
wherein the first and second deflection elements are arranged such that they are spaced apart by the at least two windows and the measuring gap.

6. The bioprocess container as claimed in claim 3, wherein the measuring gap is formed by a radiation deflection device,
wherein the radiation deflection device has at least one first deflection element and at least one second deflection element,
wherein the first and second deflection elements are arranged opposite one another and are at least regionally spaced apart from one another, so that the measuring gap is formed between the first and second deflection elements.

7. The bioprocess container as claimed in claim 6, wherein the first deflection element is designed to receive electromagnetic radiation which is emitted by the radiation-emitting element and to then deflect it to the second deflection unit such that the radiation passes through the measuring gap, and
wherein the second deflection unit is designed to receive the radiation from the first deflection unit and to then deflect it to the radiation-receiving element.

8. The bioprocess container as claimed in claim 6, wherein the first deflection element is designed to receive electromagnetic radiation which is emitted by the radiation-emitting element and to then deflect it to the measuring gap, and
wherein a radiation-receiving element is arranged below the measuring gap.

9. The bioprocess container as claimed in claim 6, wherein a face of the second deflection element that faces the measuring gap is at least regionally diffusely scattering,
wherein the first deflection element is designed to receive electromagnetic radiation which is emitted by the radiation-emitting element and to then deflect it to the measuring gap and/or the diffusely scattering face of the second deflection element, and wherein the radiation-receiving element is arranged such that it can measure the electromagnetic radiation which is reflected by the fluid to be measured and/or the diffusely scattering face.

10. The bioprocess container as claimed in claim 6, wherein the first and second deflection elements are each a prism or each have a radiation-reflecting face.

11. The bioprocess container as claimed in claim 6, wherein the first and second deflection elements are arranged on at least one window.

12. The bioprocess container as claimed in claim 1, wherein the radiation-emitting element and the radiation-receiving element are arranged at the same position below the measuring gap.

13. The bioprocess container as claimed in claim 1, wherein the measuring insert has at least one holding recess into which the radiation-emitting element or the radiation-receiving element is insertable.

14. The bioprocess container as claimed in claim 13, wherein the measuring insert comprises:
at least one holding face in which the at least one holding recess is formed and which is arranged opposite a window, a first deflection element and/or a second deflection element when insertion into the port housing has taken place, and
at least one connecting face which is connected to the at least one holding face and is designed to be connected to the port housing when insertion has taken place.

15. The bioprocess container as claimed in claim 1, wherein the measuring insert is clampable into the port housing, lockable into place with the port housing and/or screwable to the port housing.

16. The bioprocess container as claimed in claim 1, wherein the bioprocess container is a bioreactor.

17. The bioprocess container as claimed in claim 1, wherein the port housing at least partially protrudes into the interior of the container housing.

18. An optical measuring device for noninvasive spectroscopic measurement for a bioprocess container, comprising:
a port housing which is connectable to a container housing of the bioprocess container and is designed such that it is closed off from the interior of the container housing when connected;
at least one radiation-emitting element which is designed to transmit electromagnetic radiation through at least one fluid contained in the container housing;
at least one radiation-receiving element which is designed to at least partially receive the radiation which was emitted by the radiation-emitting element; and
at least one measuring insert which holds or supports the at least one radiation-emitting element and/or the at least one radiation-receiving element,
wherein the measuring insert is at least partially pushable into the port housing and is detachably connected to the port housing when pushed in.

* * * * *